United States Patent
Pisano et al.

(10) Patent No.: US 7,635,719 B2
(45) Date of Patent: Dec. 22, 2009

(54) USE OF ADAMATYL METHOXYDIPHENYL PROPENOIC ACID FOR THE TREATMENT OF ACNE

(75) Inventors: Claudio Pisano, Aprilia (IT); Loredana Vesci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 11/911,749

(22) PCT Filed: May 5, 2006

(86) PCT No.: PCT/EP2006/062088
§ 371 (c)(1),
(2), (4) Date: Nov. 26, 2007

(87) PCT Pub. No.: WO2006/122883
PCT Pub. Date: Nov. 23, 2006

(65) Prior Publication Data
US 2008/0153916 A1  Jun. 26, 2008

(30) Foreign Application Priority Data
May 20, 2005  (IT) ................... RM 2005 A 0248

(51) Int. Cl.
*A61K 31/185* (2006.01)
*C07C 63/33* (2006.01)
(52) U.S. Cl. ...................................... 514/577; 562/492
(58) Field of Classification Search .................. None
See application file for complete search history.

(56) References Cited

U.S. PATENT DOCUMENTS 5,994,330 A * 11/1999 El Khoury ................... 514/123
6,071,923 A *  6/2000 Nudelman et al. ........... 514/277
2004/0235757 A1 11/2004 Sabrina et al.

OTHER PUBLICATIONS

Cassano et al: "Studio Multicentrico in Aperto Sul Trattamento Dell' Acne Lieve/Moderata Con Adapalene in Monoterapia O in Terapia Combinata Treatment of Mild to Moderate Acne Vulgaris With Adapalene Alone or Combined With Other Anti-Acne Agents. A Multicenter Open Trial" Minerva Dermatologica, Edizioni Minerva Medica, Turin, IT, vol. 137,No. 5, 2002, pp. 369-375.

* cited by examiner

*Primary Examiner*—Paul A Zucker
(74) *Attorney, Agent, or Firm*—Lucas & Mercanti, LLP

(57) ABSTRACT

The use of a substance belonging to the class of atypical retinoids for the topical treatment of acne is described. In particular the effects on an animal model for this skin disease of a pharmaceutical or cosmetic compound for topical use containing adamantyl methoxydiphenyl propenoic acid formulated in a gel are demonstrated.

4 Claims, 1 Drawing Sheet

Microscope images (20x): Skin of rhino mice

A) untreated

B) treated with ST1898

USE OF ADAMATYL METHOXYDIPHENYL PROPENOIC ACID FOR THE TREATMENT OF ACNE

FIELD OF THE INVENTION

The invention described here relates to the use of a substance belonging to the class of atypical retinoids for the topical treatment of acne.

BACKGROUND OF THE INVENTION

Acne is a multifunctional disorder which commonly occurs during adolescence and which sometimes heals spontaneously but more often takes a long time and requires specific topical or systemic treatments with chemical substances such as benzoyl peroxide, retinoids, antibiotics and anti-androgens. Unfortunately some of these products can produce side-effects such as reddening, dryness of the skin and allergic reactions. Furthermore, one of the fundamental problems in treating acne and other skin diseases is crossing the epidermal layer, which represents the natural physiological barrier to the ingress of the drugs. Indeed to obtain a local pharmacological effect, topical application is used by administering the active principle formulated in ointments, creams or gels, used as vehicles.

Lecithin, a phospholipid of natural origin, is used in certain cosmetic or pharmaceutical preparations as the principal component or as an emulsifier. Its function, apart from being structural, can be functional in terms of carrying the active principle into the skin. Indeed the chemical similarity between lecithin (phosphatidyl choline) and the lipid components of the cell membranes suggests that vehicles based on lecithin can be well tolerated by the body and at the same time increase the pharmacological action (Scartazzini and Luisi, 1988 J. Physiol. Chem. 91, 823-833).

The term "acne" (from the Greek akni: efflorescence) describes the follicular lesions which appear during adolescence and which are linked with seborrhoea and the formation of comedones. It is an extremely common disease which, to a variable degree, affects approximately 90% of adolescents, but only 10% of these require medical intervention and only 1% of the latter pose clinical problems which are difficult to solve.

Acne is a chronic inflammation of the pilosebaceous apparatus which presents in various ways, as comedones, pustules, nodules, cysts and scars. There are many clinical varieties regarding appearance, course, age on onset and location. The most common form is juvenile acne which appears at puberty and resolves itself spontaneously around the age of 25, even though it can appear later, recur and regress after 30 years of age (Kraning et al. 1979 J. Invest. Dermatol. 73, 395-401).

Onset is generally during the age of development with typical skin lesions: comedones, papules, nodules and cysts. The comedones are follicles swollen with sebum, commonly called "whiteheads", when the follicular orifice is closed and "blackheads" when the follicular orifice opens; they are distributed with greater frequency around the nose and on it, on the forehead, around and in the ears and finally on the chin. The papules are the inflammatory complication of the comedo and appear as reddened raised areas of various sizes. They last a few days and disappear without trace. Pustules are yellowish-coloured lesions, hemispherical in shape and pus-filled, which surmount the papules. They last two to three days and voided to the outside with scab formation. Nodules are large solid formations, often painful to pressure, produced by an inflammatory infiltrate. Cysts are large raised areas filled with pus, very painful to the touch, which remain unchanged for weeks and unlike the other acne lesions can easily turn into scars, these being the permanent consequences of acne which are unaesthetic and sometimes disfiguring.

The main pathogenic factors involved in the etiopathogenesis of acne are: 1) sebaceous hypersecretion; 2) follicular hyperkeratosis; 3) bacterial colonisation of the follicles; 4) the onset of an inflammatory process. Subjects with acne secrete more sebum than the controls and this factor seemed to be correlated with the severity of the acne. The development and secretory activity of the sebaceous glands is controlled by the androgenous hormones, produced by the testicle, by the ovary and by the adrenal glands.

Testosterone influences the proliferative activity of the sebaceous gland, which has receptors with a high affinity for these hormones and also has the enzyme 5-α-reductase, capable of converting testosterone into its biological active fraction, dihydrotestosterone. The hormonal factors are involved in the cyclical flare-ups of acne during the premenstrual phase in women.

Follicular hyperkeratosis is a fundamental event for the development of the acne lesions and is due in part to the increased proliferation of the epidermis and partly to the delayed detachment of the corneocytes. The result is a thickening of the follicular wall obstructing the exit of the sebum, which then stagnates and forms comedones. Under these conditions *Propionibacterium Acnes*, an anaerobic bacterium, tends to develop and to proliferate (Strauss et al., 1974 J. Invest. Dermatol. 62, 321-325; Harris et al., 1983 J. Am. Acad. Dermatol. 8, 200-203), producing free fatty acids with irritant and comedogenic capability stimulating the immune response. Finally, inflammation is due to the passage of biologically active substances from the pilosebaceous duct to the dermis. The treatments available can be divided into keratolytic and bacteriostatic treatments if they relate to cell reconstruction and antibacterial action respectively.

The therapeutic strategies depend on the severity of the disorder. Medicines for topical use are preferred for medium or moderate forms of acne. The most common creams are those based on benzoyl peroxide, which dries out the spots and blocks infection.

There are three kinds of topical treatment for acne available today. These are based on different mechanisms of action; retinoids, comedolytic agents, which slow down the process of desquamation in order to reduce the number of comedones and microcomedones; antibiotics, with bactericidal activity which act by directly killing the forms of *P. acnes*, also having a slight indirect effect on comedogenesis; combined therapy, using both retinoids and topical antibiotics, for patients who suffer from severe forms of acne, with comedonic and inflammatory lesions at the same time.

For not particularly serious acne phenomena Retin-A, also known as tretinoin, is an anticomedonic agent which is applied directly to the skin. Its action, in the form of a lotion or cream, is keratolytic, i.e. it restores the normal process of keratin formation and prevents the formation of comedones (blackheads).

Research in the dermatological field for new therapeutic solutions is constantly evolving. The latest generation of therapeutic solutions now available are the following:

1. Tazarotene, a synthetic product which interacts specifically with the receptors of vitamin A. As well as on acne, it is effective in the treatment of psoriasis;
2. Azelaic acid has produced alternative results in European studies and is characterised by a broad spectrum of dual action, both antimicrobial and keratinising; it is in fact also used in cases of cutaneous hyperpigmentation (Graupe et al., 1996, Cutis 57, 20-35); and 3. Adapalene, a derivative of naphthoic acid with retinoidal activity. This is a modulator of cell differentiation with a keratinising effect, which is effective and less irritating than retinoic acid. It is marketed under the name Differin® and is used for the topical treatment of acne vulgaris, where comedones, papules and pustules predominate.

The international patent application WO03/011808 describes a new class of compounds defined as atypical retinoid acids which are described as having anti-tumoral use. The compounds described in this application include adamantyl methoxydiphenyl propenoic acid (ST1898).

DESCRIPTION OF THE INVENTION

The main object of the present invention relates to the discovery that adamantyl methoxydiphenyl propenoic acid has anti-acne activity in the animal model used as a reference for this disease.

This comedolytic activity could not be foreseen due to the absence of definite structural references on substances belonging to the same chemical class (adamantyl diphenylic derivatives of propenoic acid).

The main object of the present invention is therefore the use of adamantyl methoxydiphenyl propenoic acid for the preparation of a pharmaceutical or cosmetic compound for topical use for the treatment of acne.

The formula of this compound is as follows:

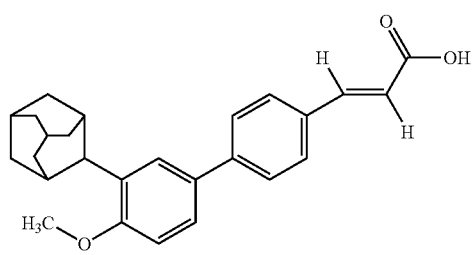

The chemical synthesis of this compound is described in the international patent application WO03/011808 (see in particular example 20).

Another object of the present invention is also a pharmaceutical or cosmetic composition for topical treatment of acne containing adamantyl methoxydiphenyl propenoic acid, as the active ingredient, together with other excipients and/or pharmaceutically acceptable vehicles.

The term "pharmaceutically acceptable" means approved by the pharmacopoeia (European, British or United States) for animal use and more particularly human use.

Examples of these excipients are: glucose, lactose, sucrose, gelatin, amide, stearates, monostearates, palmitates, glycerol, water, ethanol, lipids, phospholipids, buffered agents such as sodium dehydrogenate phosphate, or ammonium salts, mixtures of these, etc.

Other examples of excipients or vehicles are described in "Remington's Pharmaceutical Sciences" by E. Martin.

The composition of the present invention can be formulated in the form of cream, ointment, gel, foam, spray solution or sustained-release patches. The composition of the present invention is preferably in gel form.

More preferably the composition of the present invention is a lecithin gel, such as for example Epikuron 200™, which is a purified soya lecithin, i.e. a waxy phosphatidyl choline purified from soya seeds by column chromatography for use in the pharmaceutical industry (purity greater than 92%).

The quantity of active principle present in the composition of the present invention can easily be calculated on the basis of the examples reported in the present patent application and of subsequent clinical trials. The composition of the present invention preferably contains 0.1 mg of active principle per 100 mg of lecithin gel.

The invention is illustrated by the following examples which are not limitative of the scope of the invention.

EXAMPLES

Example 1

Preparation and Characterisation of the Organogels

Figure 1:
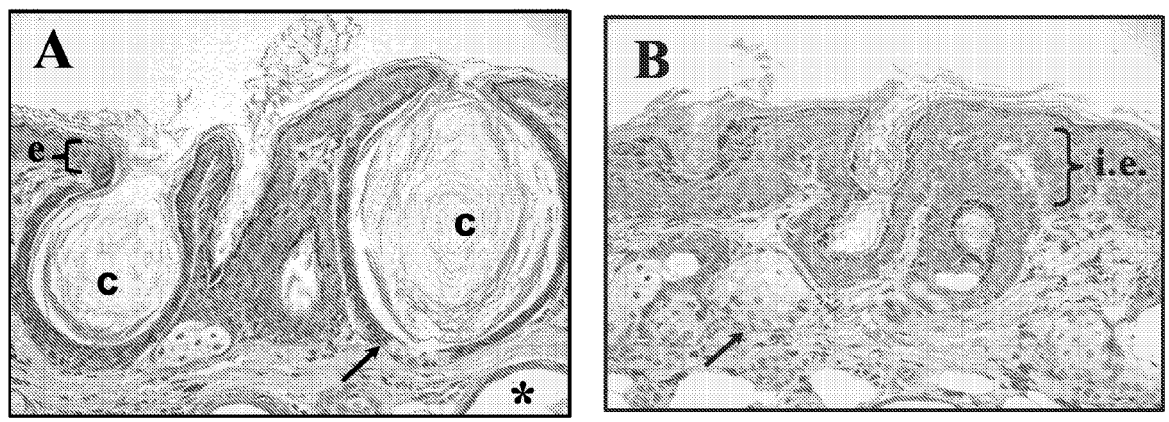
FIG. 1 shows the effects topical treatment with ST1898 (Formulation 1) on the skin of rhino mice. This treatment had a very marked effect on the reduction in the number, dimensions and horny content of the utriculi/pseudocomedones, as well as on the morphology of the sebaceous glands, which became more atrophic (arrows in FIGURE). The hyperplasia of the epidermis (B) compared with the untreated mice was also particularly clear (A). Moreover the skin of the treated rhino mice manifested a defect in the catagenic phase of the hair follicle, which involved the complete loss of the hair by the sixth week of life and the development of the so-called utriculi/pseudocomedones (C in FIG. 1), which represented models of open comedones histologically similar to the "retentional" acne lesions. The skin of rhino mice was also characterised by atrophy of the sebaceous glands (arrows in FIG. 1) and by the presence of cysts in the deep portion of the dermis (asterisk in FIG. 1 only partly visible as the images only show the most superficial portion of the skin).

The following were used for the subsequent preparations lecithin, soya seed extract (Epikuron 200™), isopropyl palmitate, ascorbic acid, ammonium molybdate, iodine crystals, tetramethylammonium phosphate, decolourising carbon and sodium dehydrogen phosphate. In addition, chloroform, methylene chloride, methanol, ethanol, dimethylsulphoxide (DMSO) and an aqueous solution of ammonia (30%).

The reference lipid POPC (1-palmitoyl-2-oleoyl-sn-glycero-3-phosphatidyl choline) was acquired from Avanti Polar Lipids (Canada) and used without further purification.

The active principle adamantyl methoxydiphenyl propenoic acid (ST1898) was synthesised and purified by Sigma-Tau (Pomezia, Rome).

Gel Preparation Method

The lecithin solution was prepared by dissolving lecithin in isopropyl palmitate (IPP), by magnetic agitation at 40-50° C., in a few minutes or a few hours depending on the percentage weight of lecithin. Every solvent-lecithin system produced a gel following the addition of a small quantity of water, generally expressed as $w_0$, indicating the molar ratio between the water and the lecithin, according to equation 1:

$$w_0 = \frac{[H_2O]}{[\text{lecithin}]} \qquad \text{Eq. 1}$$

The gel was formed when the water was completely dispersed in the organic phase, a phenomenon generally dependent on the concentration of lecithin, on the magnetic agitation and of the nature of the solvent used. Under the conditions used in this study, the gelification of the lecithin/IPP solution took place at intervals of time which ranged from a few seconds to a few minutes.

Example 2

Preparation of the Composition of ST1898—Formulation 1

Preparation of the ST1898 Formulate in the Gel Phase

The required amounts of ST1898 and Epikuron 200 lecithin were dissolved in IPP (ST1898: 0.1%, lecithin 47%, IPP 52.9%), leaving the solution under magnetic agitation for the time necessary for complete dissolution (2-12 hours, depending on the concentration of lecithin), at a temperature of 60-70° C.

All the components, including the solvent IPP, were measured gravimetrically. For practical reasons (complete dissolution of the drug) it was useful to prepare a solution of lecithin/IPP and then dissolve the drug with this organic phase. Only after this step the amount of water necessary for gelification was added. The container was protected from light by being covered in aluminium foil, given the photosensitivity of the retinoid. In the cases in which the solution did not become homogeneous immediately, it was gently irradiated. The volume of water, added using a Hamilton microsyringe, was calculated in accordance with equation 2:

$$V_{H_2O} \text{ (mL)} = \frac{m_{EP200} \text{ (g)}}{760} \times 18 \times w_0 \qquad \text{Eq. 2}$$

Where $V_{H_2O}$ represents the volume of water to be added (in ml), $m_{EP200}$ is the quantity of Epikuron 200 lecithin (in g) and $w_0$ is the desired molar ratio of water and lecithin (see eq. 1).

Example 3

Analytical Procedures

UV-Vis Analysis

UV-Vis spectrophotometry was used to characterise the retinoid ST1898 quantitatively both dissolved in the solvent DMSO and incorporated in the lecithin/IPP gel phase, using a diode array spectrophotometer (Agilent HP8452A), with a resolution of 2 nm, using 1 cm quartz cuvettes. Transferring the organogel containing the retinoid ST1898 to the cuvette required raising the temperature (approx. 60° C.), given the high viscosity of the material, followed by cooling to carry out the analysis.

HPLC Analysis

The HPLC analysis of retinoid ST1898 both dissolved in DMSO and incorporated in the gel phase, was carried out with HPLC HP1050 apparatus (Agilent), provided with a UV-Vis diode array detector and HP ChemStation software. The procedure for the quantitative analysis of the drug involves isocratic elution (methanol/water, in the volume ratio 80/20, with 0.2% of TFA) on a Reverse Phase Nucleosyl C18 column, 3 μm (particle dimensions), 125×4 mm; flow 1.5 ml/min; injected volume equal to 5 μl (under these conditions a stationary pressure of approx. 140 bar was recorded). Detection was by spectrophotometry, using absorbance (330 nm).

Typical conditions are the injection of 5 μl of solutions of ST1898 in DMSO. The retention time observed was equal to approx. 8 minutes.

The analysis of drug ST1898 incorporated in the lecithin/IPP gel phase required preliminary dilution with chloroform to reduce the viscosity of the matrix, so that it could be injected into the chromatography column. In the maximum solubility determination phase, centrifugation was used before taking the sample of gel to be analysed. The elution conditions were similar to those reported above even if the eluent flow was optimised according to the concentration of lecithin (e.g.: 1.5 ml/min.).

Typical conditions provided for the injection of ST1898 0.2% w/w in organogel of Epikuron 200 lecithin 42% w/w (approx. 800 mM) in IPP ($w_0$=3) suitably diluted in chloroform.

Quantitative Determination Via HPLC with Detection by Spectrofluorimetry.

The analysis was carried out with HPLC apparatus (System Gold, Beckham), provided with a fluorimetric detector ($\lambda_{ex}$=330 nm, $\lambda_{em}$=475 nm), isocratic elution (methanol/water, in a volume ratio 80/20, with 0.2% of TFA) on a Reverse Phase Lichrosher 100 C18 column, 5 μm (particle dimensions), 125×4 mm; flow 1.0 ml/min.; volume injected equal to 10 μl. Typical conditions involved the injection of 10 μl of solution of ST1898 in THF. The retention time observed was equal to approx. 16.5 minutes.

Example 4

Comedolytic Action of ST1898 (Formulation 1) on Epidermal Pseudocomedones in Rhino Mice Animal Model Used in the Study The rhino mouse ($hr^{rh}\ hr^{rh}$) is an allele of the hairless mouse and is an experimental animal model for non-inflammatory acne. In this animal, after the first coat of hair, a fault in the catagen phase results in a premature and irreversible hair loss at the age of 4 weeks. The follicle fails to reconstruct itself. Instead, the lower part of the original follicular unit develops into horn-producing cysts which become permanently situated in the deep dermis and enlarge as the animal ages. Meanwhile, the original pilary canals (upper part of the original follicular unit) transform into ampulliform cavities or utriculi. These utriculi are filled with horny cells and sebum and progressively enlarge due to the production and accumulation of horny material. Histologically, they resemble typical retentional acneic lesions or comedones. However, they are not visible to the naked eye and can not be squeezed out between the fingers. As in human acne, the sebaceous glands progressively shrink as the utriculi form and enlarge. Finally, the skin of the rhino mouse appears sagging and redundant, due to a paucity of elastic fibers. Therefore, the skin of adult rhino mice is characterized by the utriculi that are derived from the infundibular zone of the original follicular units. These are histologically similar to retentional acne lesions, i.e. microcomedones. Rhino mice have, therefore, been used over the last 30 years in in vivo protocols aimed at testing the comedolytic activity of new drugs, topically and to a lesser extent systemically administered, for the treatment of acne.

Comedolytic effects of various anti-acne agents, in particular retinoids administered topically, on the rhino mouse skin were first reported in the '70 using qualitative histological methods which showed: 1) the transformation of part of the utriculi/comedones in short, narrow, non-hyperplastic pilary canals with well-developed sebaceous glands, 2) the complete involution of part of the utriculi, leaving long stretches of normal appearing epidermis, 3) an increase in epidermal thickness, 4) no effect on the deep dermal cysts. These modifications begin to appear after 1 week of topical treatment with retinoids (e.g. all-trans-retinoic acid or adpalene) and reach a maximum after 3 weeks.

At present, the most widely used technique in the screening of topical comedolytic agents for evaluation and measurement of their comedolytic activity is quantitative histological image analysis of rhino mouse skin sections from a skin biopsy obtained at the end of a three week treatment period. Several microscopic measurements allow to calculate the following parameters: the total number of epidermal utriculi (comedones) per centimeter of stratum corneum length, the comedo profile which gives a measure of the morphological aspect of the comedo (i.e. ampulliform versus narrow), and the epidermal thickness.

According to the study, which brought to the present invention, male rhino mice (RHJ/LeJ), (batch No. 2004256 born on 28 Jul. 2004) and female rhino mice (batch No. 2004257, 8 born on 11 Aug. 2004 and 7 born on 21 Jul. 2004), 5-6 weeks of age with a body weight of 18-22 g at the beginning of the experiment supplied by Charles River Italy S.p.A., housed in makrolon cages (26.7×20.7×14 cm, in size); one rat to each cage, with a plastic cover with a filter and with a grill on a litter of sterile sawdust.

Food and water were available ad libitum. The daily diet of each rat involved feed (GLP 4RF21, supplied by the Mucedola company) for the entire duration of the study. The analytical certificates of the food and water of the animals were kept in the premises provided by Sigma-Tau.

The animals were housed in 12 hour light/dark cycles (7.00-19.00: light).

The parameters of the animal room were set as follows: temperature 22±2° C., relative humidity equal to 55±15%, air filters changed every 15-20 hours.

The environmental conditions were monitored and the data were kept in the Animal Housing Archives.

2 groups were formed with 6 animals in each.

The authorisation for using the animals in the Sigma-Tau laboratories was obtained from the Ministry of Health. The management and use of the animals were in accordance with European Directives Nos. 86/609 and with the Italian Regulatory system (Legislative Decree No. 116, Art. 6, 27 Jan., 1992). Each part of the study regarding the treatment of the animals was approved by Sigma-Tau's veterinary department.

Randomisation

The animal housing employee transferred the mice from the boxes to the cages at random. Each cage was then labelled with a card identifying the type of treatment (substance used, dose, route of administration and identification number of the animal).

Treatments

The animals were treated by the topical application to the back for 45 sec. of the compounds examined dosed using a 50 µl volume micropipette, once a day for 5 consecutive days per week, for a period of 3 weeks (at the Sigma-Tau laboratories). The products applied were: ST1898 0.1% in the vehicle (Formulation 1: organogel of Epikuron 200 lecithin, 46.9% w/w (approx. 800 mM) in isopropyl palmitate, with $w_0=3$) and untreated animals.

Types and Frequencies of Recordings

The animals were accurately observed, paying particular attention both to the behaviour and to the local and general signs, every day, before and after treatment, checking and recording any deaths. In addition all the animals were weighed before each treatment with the compounds under examination and with the vehicle.

Tissue Biopsies

After three days from the end of the treatment, each mouse was killed by cervical dislocation and the hair was removed from the animal's back. Biopsies were taken using 6 mm punches of the area treated, fixed in 10% buffered formalin and included in paraffin (fixing and passing through 70% ethanol at the Sigma-Tau laboratories, inclusion in paraffin at the BMC Laboratory, IDI). 3 sections were obtained from each biopsy, 3 µm thick and 150 µm apart and stained with hematoxylin-eosin stain.

Histological Examination and Analysis of the Image

Using the KS300.3 microscope, (Zeiss, Jena, Germany) with 20× magnification, a morphometric analysis and a quantitative microscopic evaluation of the following parameters were carried out:

number of utriculi/pseudocomedones per unit of length (cm) of the horny layer;

maximum diameter of the utriculi/pseudocomedones (D);

diameter of the orifice of the utriculi/pseudocomedones (d);

area of the interfollicular epidermis (S) and length (L) of the basal layer of the epidermis in the same area.

The profile of the comedones was expressed as r=d/D and the thickness of the epidermis as S/L in µm.

Evaluation of the Data

The statistical analysis of the data obtained, and more precisely the comparison between the data from the comparison of each different group of animals, was carried out using the non-parametric Mann-Whitney test for non-paired data.

Using this formulation gel (Formulation 1—ST1898 0.1% in lecithin/IPP 47/53 w/w; $w_0=3$) for experiments in vivo, it was possible to document potent comedolytic activity of the substance following topical treatment on rhino mice.

Results: Anti-Comedolytic Action of ST1898 (Formulation 1) and Adapalene on Epidermal Utriculi/Pseudocomedones of Rhino Mice.

From the literature the ability of the retinoids to induce comedolysis and thickening of the epidermis is known, effects due to a hyperproliferation of the epidermal cells (or hyperplasia) in the skin of the rhino mice (Kligman L. H. and Kligman A. M., 1979 J. Invest. Dermatol. 73, 354-8; Mezick, et al, 1984 J. Am. Acad. Dermatol. 11, 902-4; Ashton, et al, 1984 J. Invest. Dermatol. 82, 632-5).

The in vivo model used in this research project is the rhino mouse ($hr^{rh}\ hr^{rh}$), which is allelic to the mouse without hair ($hr^{hr}\ hr^{hr}$) and represents an experimental animal model for non-inflammatory acne. This model has been used for over twenty years to evaluate the therapeutic efficacy, in particular comedolytic efficacy, of anti-acne compounds applied topically and also administered systemically. The rhino mice manifested various skin changes, including a defect in the catagenic phase of the hair follicle which involved the complete loss of the hair by the sixth week of life and the development of the so-called utriculi/pseudocomedones (C in FIG. 1), which represented models of open comedones histologically similar to the "retentional" acne lesions. The skin of rhino mice was also characterised by atrophy of the sebaceous glands (arrows in FIG. 1) and by the presence of cysts in the deep portion of the dermis (asterisk in FIG. 1 only partly visible as the images only show the most superficial portion of the skin).

ST1898 (Formulation 1) applied topically, had pharmacologically useful characteristics for treating acne, with a comedolytic and anti-inflammatory effect and leading to a reduction in the number of comedones. ST1898 therefore acted as a modulator of the cell differentiation processes of keratinisation and inflammation which in acne pathology are greatly changed (FIG. 1).

As it can be seen in FIG. 1, the topical treatment of the skin of rhino mice with ST1898 (Formulation 1) had a very marked effect on the reduction in the number, dimensions and horny content of the utriculi/pseudocomedones (Table 1), as well as on the morphology of the sebaceous glands, which became more atrophic (arrows in FIGURE). The hyperplasia of the epidermis (B) compared with the untreated mice was also particularly clear (A).

TABLE 1

Analysis of the images of the epidermal parameters on the skin of male and female rhino mice.

| Treatments | No. of | Comedones[a] (cm | Comedo profile (r = | Thickness of (μM |
|---|---|---|---|---|
| Untreated | 6 | 27.8± | 0.65± | 23.5± |
| ST1898 0.1% | 6 | **7.5± | **1.01± | **82.7± |

The data are the mean ± SD.
*$P < 0.05$ and **$P < 0.01$ vs. the untreated group (Mann-Whitney).
[a]number of comedones per length of horny layer expressed in cm.

The parameter directly correlated to the comedolytic effect of a drug following topical treatment of acne is r (Tab. 1) (Mezick, et al, 1984 J. Am. Acad. Dermatol. 11, 902-4; Bouclier, et al., 1991 Skin Pharmacol. 4, 65-73): if r is equal to or greater than 1, the compound under examination has a comedolytic effect demonstrated by the reduction in the number of typical acne lesions.

Compared with the control represented by the group of untreated mice, it can be seen that the value of this parameter is changed by ST1898 (Formulation 1) which produced the change from closed comedones to open comedones with a value of r equal to 1, demonstrating a powerful comedolytic effect. In addition, in the histograms it can be seen that the parameter which describes the epidermal thickness increases following treatment with ST1898.

Example 5

Preparation of the Composition of ST1898—Formulation 2—Preparation of the ST1898 Formulate in the Gel Phase Formulations: ST1898 0.1 and 0.05% in the vehicle.
Vehicle: carbomer 980, propylene glycol, poloxamer, disodium edentate, methyl hydroxybenzoate, phenoxyethanol, sodium hydroxide and purified water).
Negative control: no treatment.
Adapalene (Differin Gel®) was used as reference compound (0.1%).

Example 6

Comedolytic Action of ST1898 (Formulation 2) on Epidermal Pseudocomedones in Rhino Mice The authorization to use animals in Sigma-tau laboratories was obtained by Italian Health Authority. The Care and Husbandry of animals were in accordance with European Directives no. 86/609, and with Italian DL 116, Jan. 27, 1992. All parts of this study concerning animal care have been approved by the official sigma-tau Veterinarian.

Animal Supply and Husbandry

The mice (Charles River Italy S.p.A. for the Jackson Laboratory) were housed inside cages of makrolon (26.7×20.7×14 cm) (1 mouse/cage) with grating cover of steel and bedstead of sawdust of pulverized and sterilized dust-free bedding cobs. Animals were housed under a light-dark cycle, keeping temperature and humidity constant. Parameters of the animal rooms were assessed as follows: 22±2° C. temperature, 55±15% relative humidity, about 15-20 filtered air changes/hour and 12 hour circadian cycle of artificial light (7 a.m., 7 p.m.). The environmental conditions were monitored; the data were retained in Animal Housing Archives.

Diet and Water Supply

Drinking water was supplied ad libitum. Each mouse was offered daily a complete pellet diet (GLP 4RF21, Mucedola) throughout the study. The analytical certificates of animal food and water were retained at Sigma-Tau premises.

Study Design—Treatment of Mice 30 rhino (RHJ/LeJ) mice (Jackson Laboratory), 15 male and 15 female (6-8 weeks of age) were subdivided in 6 mice/group. Two groups were treated with ST1898 (Formulation 2) (0.1% and 0.05% in the vehicle), a group with adapalene (Differin® gel), used as reference compound (0.1%), a group with the vehicle (the same of the formulation of Differin® gel: carbomer 980, propylene glycol, poloxamer, disodium edentate, methyl hydroxybenzoate, phenoxyethanol, sodium hydroxide and purified water).

A group was not treated (control). The drugs (50 μl) were applied with a sterile gloved finger topically on the dorsal skin (massage for 30-45 sec), once daily for 5 consecutive days/week (excluding Saturdays and Sundays) for 3 consecutive days. Three days after the last application, mice were sacrificed by cervical dislocation. Two skin punch biopsies (6 mm) were taken immediately after death from all sacrificed animals. The biopsies were formalin-fixed (10% buffered formalin solution) and paraffin-embedded.

Post Mortem Examination

Quantitative histological image analysis was evaluated as the total number of epidermal utriculi (comedones) per centimeter of stratum corneum length, the comedo profile, and the epidermal thickness. From one biopsy, three 3-μm thick skin sections were obtained at 150 μm intervals and were stained with hematoxylin-eosin. The second biopsy was kept stored for records.

Assisted computer morphometric analysis of the stained skin sections was performed using a Zeiss KS300.3 system (parameters n. 1, 3 and 4). For total length of the stratum corneum measurement a micrometric equipment was used. The following microscopic parameters were measured:

1) on each open epidermal utriculum/comedo the largest diameter or diameter taken at half depth (D) and diameter of the surface orifice (d), 2) length of the three sections, taken as total length of the stratum corneum, 3) total number of epidermal utriculi/comedones in the three sections, 4) in interfollicular areas, surface (S) of the epidermis and length (L) of the corresponding basal layer.

From these data the following mean (+/−SD) values were calculated for each group of animals:

1) number of utriculi/(comedones)/length of stratum corneum (cm);

2) Comedo profile, calculated as r=d/D, 3) epidermal thickness, calculated as S/L in □m.

Administration of Test Item

A topical application on the dorsal skin (massage for 30-45 sec) was performed of 50 μl applied with a gloved finger. The treatment was done once daily for 5 consecutive days/week (excluding Saturdays and Sundays) for 3 consecutive weeks.

Data Analysis

Statistical analysis was performed using the two-tailed Student's "t" test to compare data obtained from the different groups of animals.

A significant difference was considered when a p value (P)≦0.05 was reached.

Other statistical methods were used if it was considered necessary.

Results

During the treatment, the body weight of mice was recorded to control the healthy status of mice. No significative variation in body weight was found (table 2).

The results of the analysis of rhino mice treated with ST1898 (Formulation 2) and of control mice are reported in table 2 and in FIGS. 1-8. The most relevant findings are summarized hereafter.

Histological Analysis

The analysis of the histologic specimens from the five groups of rhino mice showed:

a) no effect of the vehicle treatment on the utricoli (comedones) number and morphology and on the epidermal morphology and thickness, as compared to untreated skin. Numerous, enlarged comedones filled with cornified cells were observed in all specimens. Sebaceous glands appeared markedly atrophic. The scant interfollicular epidermis of untreated and vehicle-treated mice comprised a single layer of basal cells, two to three layers of spinous cells and one layer of granular cells containing keratohyaline granules. The stratum corneum appeared thick and loosely organized, with a characteristic "basket wave" appearance.

b) a strong reduction in the number of comedones in the skin of mice treated with ST1898. Such effect appeared comparable in mice treated with ST1898 and adapalene-treated mice. In all active compound-treated animals, most follicles became narrow pilary canals which did not show accumulation of horny material. In addition, distinctly enlarged sebaceous glands were connected to the follicular canals.

c) a hyperplasia of interfollicular epidermis in ST1898-treated and adapalene-treated mice. Specifically, interfollicular epidermis comprised a single layer of basal cells, 3-6 layers of spinous cells and 3-5 layers of granular cells containing numerous, large keratohyaline granules. The stratum corneum was more compact, in particular in its lower portion. Of note, epidermal hyperplasia appeared more marked in the skin of adapalene-treated mice as compared to ST1898-treated mice. In addition, a mild dermal lymphocyte infiltrate was observed in all active compound-treated animals.

Morphometric Analysis

Number of comedones. The number of comedones per centimeter of stratum corneum was comparable in untreated mice and mice treated with the vehicle.

This value was highly reduced in ST1898 0.1% and 0.05%-treated mice as compared to untreated and vehicle-treated controls (p value<0.0005). The number of comedones was significantly lower in 0.1% ST1898-treated mice with respect to 0.05% ST1898-treated mice (p value<0.005). ST1898 0.1% and adapalene 0.1% showed a comparable effect (p value=0.288626).

Comedo profile. The analysis of comedo profile showed a highly significant and comparable increase in the r value in 0.1% ST1898-, 0.05% ST1898- and adapalene-treated mice with respect to untreated and vehicle-treated control mice (p value<0.0005). These last two groups showed comparable values.

Epidermal thickness. The epidermal thickness was significantly increased in ST1898 0.1%-, ST1898 0.05%- and adapalene-treated mice with respect to both groups of control mice (p value<0.0005). Untreated and vehicle-treated mice showed comparable values. The thickness of the epidermis was higher in ST1898 0.05%-treated mice as compared to mice treated with 0.1% ST1898 (p value<0.05) or adapalene (p value<0.005). Adapalene-treated mice showed a significantly thicker epidermis when compared with mice treated with 0.1% ST1898 (p value<0.05).

CONCLUSION

The analysis of rhino mice topically treated with the retinoid ST1898 for 3 consecutive weeks (once daily for 5 days/week) revealed that ST1898 at both concentrations used (0.1% and 0.05%) showed comedolytic and anti-comedogenic activity, as assessed by (i) the highly reduced number of comedones compared with untreated or vehicle-treated mice, and (ii) the strong increase in narrow comedones (increased r value).

ST1898 exerted a similar effect to that elicited by the reference compound, adapalene, on both comedo number and profile, when administered at the same concentration (0.1%).

The effect of ST1898 was dose-related, being 0.05% ST1898 less effective than 0.1% ST1898 in reducing the number of comedones and in inducing epidermal hyperplasia.

Moreover, epidermal hyperplasia was significantly reduced following ST1898 0.1% topical treatment as compared with reference compound treatment, showing a possible advantage in using ST1898 over presently available topical retinoids.

TABLE 2

Body weight and lethality of rhino mice treated with ST1898 (Formulation 2) or adapalene according to the schedule qdx5/wx3w

| Treatment | n | Initial body weight gr ± SE | Final body weight gr ± SE | Body weight loss max (%) |
|---|---|---|---|---|
| Control (no treated) | *5 | 20.7 ± 1.3 | 22.8 ± 1.2 | 0 |
| Vehicle | *5 | 21.5 ± 0.9 | 22.9 ± 1.3 | 1 |
| ST1898 0.1% | 6 | 20.9 ± 0.4 | 21.9 ± 0.5 | 1 |
| ST1898 0.05% | 6 | 20.9 ± 1.0 | 22.2 ± 1.1 | 0 |
| Adapalene 0.1% (Differin gel ®) | *5 | 21.3 ± 1.1 | 21.2 ± 1.3 | 4 |

*One mouse was exluded from the study before starting the treatment for the low body weight.

Mice were sacrificed 3 days after the last treatment. The vehicle used for ST1898 (Formulation 2) was the same of Differin gel (carbomer 980, propylene glycol, poloxamer, disodium edentate, methyl hydroxybenzoate, phenoxyethanol, sodium hydroxide and purified water).

Morphometric Analysis of the Skin of ST1898 (Formulation 2)-Treated and Control Mice (results are expressed as mean value±SD)

TABLE 3.1

| Treatments | Comedones (n/cm) | P value vs untreated | P value vs vehicle |
|---|---|---|---|
| Untreated | 57.35 ± 4.96 | | 0.982154 |
| Vehicle | 57.27 ± 5.74 | 0.982154 | |
| ST1898 0.1% | 31.35 ± 5.37 | $1.68 \times 10^{-5}$*** | $2.89 \times 10^{-5}$*** |
| ST1898 0.05% | 42.42 ± 4.5 | 0.00056** | 0.00098** |
| Adapalene 0.1% | 28.31 ± 2.92 | $3.41 \times 10^{-6}$*** | $8.12 \times 10^{-5}$*** |

P value 0.1% ST1898 vs 0.05% ST1898 = 0.003182**
P value 0.1% ST1898 vs adapalene = 0.288626
P value 0.05% ST1898 vs adapalene = 0.000213***

TABLE 3.2

| Treatments | Comedo profile (r = d/D) | P value vs untreated | P value vs vehicle |
|---|---|---|---|
| Untreated | 0.62 ± 0.05 | | 0.918704 |
| Vehicle | 0.61 ± 0.05 | 0.918704 | |
| ST1898 0.1% | 1.27 ± 0.07 | $2.85 \times 10^{-8}$*** | $2.99 \times 10^{-8}$ |
| ST1898 0.5% | 1.26 ± 0.13 | $3.24 \times 10^{-6}$*** | $3.29 \times 10^{-6}$*** |
| Adapalene 0.1% | 1.24 ± 0.11 | $3.22 \times 10^{-6}$*** | $3.23 \times 10^{-6}$*** |

P value 0.1% ST1898 vs 0.05% ST1898 = 0.794536
P value 0.1% ST1898 vs adapalene = 0.517798
P value 0.05% ST1898 vs adapalene = 0.792654

TABLE 3.3

| Treatments | Epidermal thickness (μm) | P value vs untreated | P value vs vehicle |
|---|---|---|---|
| Untreated | 20.90 ± 2.91 | | 0.857119 |
| Vehicle | 20.56 ± 2.86 | 0.857119 | |
| ST1898 0.1% | 42.52 ± 2.17 | $1.89 \times 10^{-7}$*** | $1.50 \times 10^{-7}$*** |
| ST1898 0.05%% | 37.45 ± 3.97 | $2.94 \times 10^{-5}$*** | $2.0 \times 10^{-5}$*** |
| Adapalene 0.1% | 57.33 ± 9.99 | $5.09 \times 10^{-5}$*** | $4.72 \times 10^{-5}$*** |

P value 0.1% ST1898 vs 0.05% ST1898 = 0.020697*
P value 0.1% ST1898 vs adapalene = 0.006037*
P value 0.05% ST1898 vs adapalene = 0.001479**
*= $p < 0.05$;
**= $p < 0.005$;
***= $p < 0.0005$

The invention claimed is:

1. Pharmaceutical or cosmetic gel composition for topical use for the treatment of acne containing adamantyl methoxydiphenyl propenoic acid, as the active principle, and excipients and/or pharmaceutically acceptable vehicles; said vehicles and/or excipients containing lecithin.

2. Composition according to claim 1, containing 0.1 mg of adamantyl methoxydiphenyl propenoic acid per 100 mg of gel.

3. A method of treating acne, comprising topically applying the composition of claim 1 to the affected area of skin requiring the same.

4. A topical gel composition for the treatment of acne, comprising 0.1 mg of adamantyl methoxydiphenyl propenoic acid per 100 mg of gel, and excipients and/or pharmaceutically acceptable vehicles; said vehicles and/or excipients containing lecithin.

* * * * *